United States Patent [19]
Eklund et al.

[11] Patent Number: 6,165,776
[45] Date of Patent: Dec. 26, 2000

[54] **SELECTIVE AND DIFFERENTIAL MEDIUM FOR ISOLATION OF *LISTERIA MONOCYTOGENES***

[75] Inventors: Mel W. Eklund; Frank T. Poysky; Rohinee N. Paranjpye; Laura C. Lashbrook; Mark E. Peterson; Gretchen A. Pelroy, all of Seattle, Wash.

[73] Assignee: The United States of America as represented by the Secretary of Commerce, Washington, D.C.

[21] Appl. No.: 08/220,212

[22] Filed: Mar. 30, 1994

[51] Int. Cl.$^7$ .................................................. C12N 1/20
[52] U.S. Cl. ...................... 435/253.6; 435/34; 435/252.1
[58] Field of Search .................................. 435/253.6, 34, 435/252.1

[56] References Cited

U.S. PATENT DOCUMENTS

| | | | |
|---|---|---|---|
| 5,145,786 | 9/1992 | Bailey et al. | 435/252.4 |
| 5,187,070 | 2/1993 | Fung et al. | 435/25 |

OTHER PUBLICATIONS

N. Al–Zoreky et al, *Applied and Environmental Microbiology*, Oct. 1990, p. 3154–3157, "Highly Selective Medium for Isolation of *Listeria monocytogenes* from Food".

M. Peterson et al, *Journal of Food Protection*, vol. 56, No. 11, pp. 938–943, Nov. 1993, "Parameters for Control of *Listeria monocytogenes* in Smoked Fishery Products . . . ".

E. Bannerman et al, *Applied and Environmental Microbiology*, Jan. 1988, pp. 165–167, "A New Selective Medium for Isolating Listeria spp. from Heavily Contaminated Material".

M. Blanco et al, *Letters in Applied Microbiology*, 1989, pp. 125–128, "A technique for the Direct Identification of Haemolytic–pathogenic Listeria on Selective Plating Media".

P.K. Cassiday et al, *Food Microbiology*, 1989, pp. 113–125, "Evaluation of Ten Selective Direct Plating Media for Enumeration of *Listeria monocytogenes* in Hams and Oysters".

L.J. Cox et al, *Food Microbiology*, 1991, pp. 37–49, "Enhanced Haemolysis agar (EHA)–an Improved Selective and Differential Medium for Isolation of *Listeria monocytogenes*".

G.D.W. Curtis et al, *Letters in Applied Microbiology*, 1989, pp. 95–98 "A selective differential medium for the isolation of *Listeria monocytogenes*".

R. Lachica, *Applied and Environmental Microbiology*, Jan. 1990, pp. 167–169, "Selective Plating Medium for Quantitative Recovery of Food–Borne *Listeria monocytogenes*".

W.H. Lee, 1989, U.S. Department of Agriculture, Agricultural Research Service, personal communication.

W.H. Lee et al 11, *Applied and Environmental Microbiology*, Nov. 1986, pp. 1215–1217, "Improved *Listeria monocytogenes* Selective Agar".

M.E. McBride, et al, *J. Lab & Clin. Med.*, Jan. 1960, 00. 153–157, "A Selective Method for the Isolation of Listeria Monocytogenes From Mixed Bacterial Populations".

D. McClain et al, 1988, Development of USDA–FSIS Method for Isolation of *Listeria monocytogenes* from Raw Meat and Poultry, pp. 660–664.

P. Van Netten et al, *International Journal of Food Microbiology*, 8:pp. 1215–1217, 1989, "Liquid and Solid Selective Differential Media for the Detection and Enumeration of *L. monocytogenes* and other Listeria spp.".

P.K. Cassiday et al, *Journal of Food Production*, vol. 52, No. 3, pp. 207–214, Mar. 1989, Methods and Media to Isolate and Enumerate *Listeria monocytogenes*: A Review.

F.T. Poysky, et al *Journal of Food Production*, vol. 56, No. 4, pp. 326–332, Apr. 1993, Selective and Differential Medium for Isolation of *Listeria monocytogenes* from Foods.

*Primary Examiner*—Irene Marx
*Attorney, Agent, or Firm*—Stevens, Davis, Miller & Mosher, L.L.P.

[57] ABSTRACT

Esculin-free hemolytic Ceftazidime lithium chloride agar (HCLA) as a selective and differential medium specific for the isolation of *Listeria monocytogenes*. The medium also contains red blood cells.

13 Claims, No Drawings

SELECTIVE AND DIFFERENTIAL MEDIUM FOR ISOLATION OF *LISTERIA MONOCYTOGENES*

BACKGROUND OF THE INVENTION

1. Field of the Invention

The present invention relates to a plating medium as a selective and differential medium for the isolation of *Listeria monocytogenes*.

2. Background Art

*Listeria monocytogenes* is a gram positive, motile, aerobic and facultatively anaerobic bacterium which is ubiquitous in nature. It can cause various diseases in man including meningoencephalitis, low-grade septicemia, infectious mononucleosis-like syndrome, pneumonia, endocarditis, bacterial aortic aneurysm, localized abscesses, papular or pustular cutaneous lesions, conjunctivitis and urethritis. In the past decade, *Listeria monocytogenes* have been recognized as a major foodborne pathogen. Outbreaks of listeriosis have been linked to a number of contaminated foods such as coleslaw, Mexican-style soft cheese, pasteurized milk and turkey franks. It has been isolated from fresh produce, dairy products, processed meats and seafood products. About 500 people die each year in the United States from Listerial food poisoning; the victims are usually the immunocompromised, pregnant women and neonates.

Because of the pernicious effects of this pathogen and its increasing presence in human foods, there is a need for a quick and reliable method for selectively determining the presence of the subject bacterium in a food sample.

The real challenge to a food microbiologist is to be able to recover small numbers of the subject bacterium from food products and identify its presence even though such food products often contain large numbers of a variety of other bacteria.

A prior accepted assay for *L. monocytogenes* is described in "FSIS Method for the Isolation and Identification of *Listeria monocytogenes* From Processed Meat and Poultry Products", Laboratory Communication No. 57, May 24, 1989, distributed by the USDA and others; this publication is incorporated herein by reference. Broadly speaking, the FSIS assay involves placing a sample of meat in UVM (University of Vermont) Broth followed by incubation at 30° C. for 24 hours. A 0.1 ml aliquot of the incubated mixture is then placed in 10 ml of Fraser Broth and incubated at 30° C. for 24–48 hours. If the Fraser Broth darkens, the liquid is swabbed onto a modified Oxford agar plate, which is then incubate at 35° C. for 24–48 hours. The incubated plates are then examined for Listeria species colonies exhibiting characteristic surrounding black zones resulting from hydrolyzed esculin. All suspected Listeria species form black colonies on Oxford or modified Oxford medium. Black colonies or Listeria colonies are then gently touched with an inoculation needle and are streaked for isolation onto a Horse Blood Overlay Agar plate. These plates are incubated overnight at 35° C. Thereafter, the plates are examined under a fluorescent lamp and translucent colonies with a narrow zone of beta hemolysis surrounding such colonies are then further screened and subjected to conventional confirming tests.

Generally speaking, the prior *L. monocytogenes* assay involves a total time of from 56–72 hours. This represents a real difficulty for the food processor, in that food otherwise ready for shipment must be held pending the completion of assay screening. Accordingly, there is a real need in the art for an effective assay for *L. monocytogenes* (or other motile facultative anaerobic pathogens) which can be successfully performed in a significantly shorter period of time.

There are also known media with agar bases which we disclosed as being effective for the selective isolation of *L. monocytogenes*. However, such media actually are only selective for Listeria and additional process steps are required to further identify and select for *L. monocytogenes*. One such medium is Oxford Formulation which is based on the formulation described by Curtis et al, "A Selective Differential Medium for Isolation of *Listeria monocytogenes*", Letters in Applied Microbiology, 1989, 8, 95–98, herein incorporated by reference.

Oxford Formulation utilizes (i) the selective inhibitory components of lithium chloride, acriflavine, colistin sulphate, cefotetan, cycloheximide and fosfomycin and (ii) the indicator system esculin and ferrous iron for the isolation and differentiation of Listeria from clinical and food specimens. Listeria species hydrolyse esculin, producing black zones around the colonies. The blackening is caused by the hydrolysis of the glycoside esculin to glucose and the aglycone aesculetin, the latter forming an insoluble black complex with the iron present in the medium as ferric citrate. Gram-negative bacteria are inhibited. Most unwanted gram-positive species are suppressed, but some strains of Enterococci grow poorly and exhibit a weak esculin reaction, usually after 40 hours of incubation. Some Staphylococci may grow as esculin-negative colonies. A separate step would be required to further differentiate Listeria species from one another.

Lee's Modified Oxford Formulation (LMO) includes the addition of moxalactam after autoclaving the agar base of Oxford Formulation. The introduction of moxalactam eliminated the growth of Staphylococci.

McBride Listeria agar (MLA) is comprised of phenylethanol agar base (Difco), lithium chloride, glycine and blood. Phenylethanol and lithium chloride are inhibitory to gram negative organisms. It is also reported that phenylethanol inhibits repair of heat-injured cells of Listeria. Therefore this medium may inhibit the growth of Listeria.

LiCl Phenylethanol Moxolactam agar (LPM) is similar in composition to MLA except there is a ten-fold increase in lithium chloride, and glycine anhydride is substituted for glycine; blood is omitted from this formulation. Glycine has been found to inhibit *L. monocytogenes*.

Another medium, (PALCAM), containing Ceftazidime as well as polymyxin B, acriflavine, lithium chloride, esculin, ferric ammonium citrate, mannitol and phenyl red is used to recover *L. monocytogenes*.

McClain and Lee, "Development of USDA-FSIS Method for Isolation of *Listeria monocytogenes* from Raw Meat and Poultry", J. Assoc. Off. Anal. Chem. (1988) 71:660–664 (herein incorporated by reference) developed a method to detect naturally occurring *L. monocytogenes* in meat. The method uses two stages: (1) LPM Formulation (supra) and (2) a thin-layer horse blood agar plate (HL) for detection of β-hemolytic Listeria. The method identifies Listeria colonies in 3–4 days.

Recently, a blood overlay technique was described by Blanco et al, "A Technique for the Direct Identification of Hemolytic Pathogenic Listeria on Selective Plating Mechanism", Lect. Appl. Microbiol. Vol. 9, pp. 125–128 (1989) and Cox et al, "Enhanced Haemolyses Agar (EHA)—An Improved Selective and Differential Medium for Isolation of *Listeria monocytogenes*", Food Microbiol 8:37–49. Blanco's medium requires 64 hours of total incubation with an overlay of blood agar made at 48 hours. The medium of Cox utilizes sphingomycelinase to enhance lysis of ovine erythrocytes. This medium requires 48 hours of incubation.

U.S. Pat. No. 5,187,070 to Fung et al, herein incorporated by reference, discloses a method of first incubating the sample in growth medium containing esculin which will change color in the presence of Listeria. Once a color change is observed, the subject bacterium is given an effective amount of a growth stimulating substance, such as oxyrase enzyme. Identification of the bacterium requires 24–36 hours. In addition to requiring additional steps neessary to further identify L. monocytogenes, it is reported by Cox et al, supra, that "hydrolysis of esculin could give rise to acid formation from liberated glucose and lead to spurious results."

Thus the need for a rapid and accurate confirmation method for the presence of L. monocytogenes in a food product and the suppression of background flora is widely recognized.

The invention herein, a new agar formulation devoid of esculin allows for the identification of L. monocytogenes and the differentiation thereof from background flora in 17–24 hours.

SUMMARY OF THE INVENTION

Investigations of the incidence of Listeria spp. in fishery products and the need for a more rapid presumptive test for L. monocytogenes has prompted the formulation of a new selective and differential medium. HCLA (hemolytic Ceftazidime lithium chloride agar) medium of the present invention relies on the defined β-hemolytic characteristics of L. monocytogenes and the bacterium's resistance to the antibiotic Ceftazidime, lithium-chloride, and colistin. The characteristic β-hemolysis of Listeria monocytogenes is readily 3 recognized within 17 to 24 h incubation and Listeria monocytogenes colonies can be differentiated from numerous colonies of other Listeria species, such as non-hemolytic Listeria innocua.

Advantages of the invention include rapid and accurate identification, no secondary transfer to another medium, and use of ambient light sources instead of special lighting conditions to identify β-hemolytic zones. Magnifying equipment is not needed to identify L. monocytogenes, and the procedures using the media of the present invention require no special enrichment procedures. A hemolytic enhancer is not necessary, and the invention can be used to detect L. monocytogenes in a host of foods and food products even in the presence of large populations of other non-hemolytic Listeria organisms.

DETAILED DESCRIPTION OF THE INVENTION

The medium of the present invention is a modification of Lees modified Oxford Formulation (supra) LMO and a non-selective horse blood overlay agar (HL) of McClain and Lee (supra). More specifically, the invention uses a base layer of agar, lithium chloride, an iron source, such as ferric ammonium citrate, antibiotics such as Colistin and Ceftazidime, with a thin blood agar overlay poured on top of the base layer. The blood layer includes all of the ingredients discussed above and includes horse blood.

A particular formulation of the invention, for illustration, is shown below in Table 1.

TABLE 1

Isolation Agar (HCLA) for Listeria monocytogenes

| Component | Concentration | |
| --- | --- | --- |
| (Difco-Bacto) Columbia blood agar base | 39 g/L | |
| (Difco-Bacto) agar | 5 g/L | |
| (Sigma L0505) Lithium chloride anhydrous | 7.5 g/L | |
| (Sigma F5879) Ferric ammonium citrate | 0.5 g/L | |
| (Sigma C1511) Colistin, methane sulfonate I.U. = 11,500/mg | 10 g/L | |
| (Eli Lilly III0814) Ceftazidime acid pentahydrate | 20 mg/L | |
| Final pH | 7.0 | |
| Base layer | 10 ml | No horse blood |
| Overlay | 5 ml | 4% horse blood |

L. monocytogenes selectively cultured on the surface of the overlay will lyse the blood in the overlay creating clear colorless zones surrounding the colonies, easily visible when light, from a normal light or ambient source such as a window transmitting light, desk lamp, etc., is transmitted to the bottom of petri dishes holding the medium.

The following procedure is used to select and isolate L. monocytogenes in a food source.

A. Enrichment Procedure

Twenty-five g portions of each test sample were inoculated into 225 ml Listeria Enrichment Broth (LEB) used by the FDA and University of Vermont (UVM) broth used by the USDA Food Safety and Inspection Service (FSIS). After 24–48 h incubation at 30° C. a 0.1 ml portion from each enrichment broth was plated on selective agars. With the USDA enrichment method, McClain and Lee's modification of UVM was used when testing extended beyond 24 h. In this procedure, a 0.1-ml portion from UVM was inoculated into 10 ml of UVM-2 which has an increased concentration of acriflavine.

B. Selective Plating Agars

HCLA—Hemolytic Ceftazidime Lithium Chloride Agar: The formula for this medium is shown in Table 1. As discussed, this medium is a modification of LMO and HL of McClain and Lee. The agar was autoclaved at 121° C. for 12 min. After cooling to 46° C., 5 ml of a filter-sterilized solution of Ceftazidime acid pentahydrate in 0.1 M phosphate buffer (pH 7.0) was added to a final concentration of 20 mg/L. Plates were made with a 10 ml base layer and soon after solidifying were overlaid with 5 ml of the same agar to which 4% horse blood (at 20° C.) had been added.

As a comparison, Oxford Formulations and LMO Formulations were also prepared, and streaked with L. monocytogenes from the enrichment broth.

OX and LMO were incubated at 30° C., and HCLA plates were incubated at 35° C.

COMPARATIVE EXAMPLE 1

Comparison of HCLA, OX, and LMO Media

L. monocytogenes formed blue-gray and occasionally white colonies surrounded by distinct zones of β-hemolysis on HCLA within 17–24 h of incubation. The colony characteristics were readily observed with transmitted light; without the aid of any oblique lighting systems or magnifying lenses. Individual colonies of L. monocytogenes were easily distinguishable by their blue-gray color and narrow zones of beta hemolysis from hundreds of colonies of L. innocua, which were always non-hemolytic on HCLA medium. In contrast, L. monocytogenes could not be distinguished from other Listeria species on OX or LMO because all species produce black colonies on those media.

HCLA was compared with LMO and OX agar for recovery of L. monocytogenes from UVM or LEB enrichments of fishery products, by inoculating 0.1 ml from each enrichment onto the surface of each medium and incubating for 24 h at 35° C. All hemolytic colonies from HCLA were selected and identified when there were less than 16 per plate. When there were larger populations, 16 hemolytic colonies were randomly selected. Sixteen black colonies were randomly selected from all OX and LMO plates. Typical results are shown in Table 2. All of the hemolytic colonies from HCLA were identified as L. monocytogenes. In comparison, the inability to differentiate Listeria species on OX and LMO resulted in L. monocytogenes being identified only a small percentage of the time, particularly in samples where large populations of L. innocua were present.

To determine how many colonies of L. monocytogenes were actually present on the three different media, the colonies were replicated onto HL agar following procedures of Cassiday et al, "Replicating of Colonies from Listeria—Selective Agar to Blood to Improve the Isolation of Listera monocytogenes from Foods." Appl. Environ. Microbiol. (1990) 56:2274–2275. No additional colonies produced hemolysis on HL agar when they were transferred from HCLA medium. Numerous hemolytic colonies, undetected during random selection from OX and LMO, were observed and identified as L. monocytogenes, when the entire population was replicated onto HL medium (Table 2).

TABLE 2

| Replicate No. | Sample No. | Selective Media | | |
|---|---|---|---|---|
| | | HCLA | OX | LMO |
| 1 | 697 | 3/3[a] (3)[b] | 0/16 (3) | 1/16 (5) |
| | 698 | none detected | none detected | none detected |
| | 699 | 16/16 (75) | 0/16 (40) | 1/16 (54) |
| | 700–707 | none detected | none detected | none detected |
| | 708 | TNTC[c] | TNTC | TNTC |
| | 709 | 16/16 (60) | 2/16 (35) | 0/16 (55) |
| 2 | 6601 | 16/16 (19) | 0/16 (13) | 0/16 (19) |
| | 6602 | 16/16 (27) | 1/16 (25) | 2/16 (36) |
| | 6003 | 16/16 (26) | 2/16 (18) | 3/16 (15) |
| | 6604 | 16/16 (21) | 3/16 (19) | 2/16 (31) |
| | 6605 | 16/16 (27) | 0/16 (21) | 2/16 (20) |
| | 6606 | 11/11 (11) | 0/16 (9) | 1/16 (12) |

[a]Results are expressed as number of colonies of L. monocytogenes per number of colonies tested. All hemolytic colonies from HCLA were tested when there were 16 or less per plate. When there were more than 16 hemolytic colonies, only 16 were tested. Sixteen black colonies were selected from all OX and LMO plates.
[b]Number in parentheses represents number of colonies that were hemolytic and identified as L. monocytogenes when all the colonies from selective media were replicated onto HL plates.
[c]TNTC = colonies on plate were "too numerous to count".

The preferred medium composition of the invention was obtained by modifying the components of the composition based on the results of the following experiments:

EXPERIMENT 1

Effects of Esculin and Ferric Ammonium Citrate

As noted above, esculin and ferric ammonium citrate have been added to various media to differentiate Listeria from other microorganisms. Listelia spp. hydrolyze esculin to glucose and aglycone aesculetin, which forms a complex with the iron from ferric ammonium citrate, resulting in black colonies with black haloes.

When ferric ammonium citrate was added to HCLA, it enhanced growth of all Listeria species and it enhanced β-hemolysis of L. monocytogenes. The addition of esculin by itself, however, inhibited β-hemolysis. When the combination of esculin and ferric ammonium citrate was tested, the blackened colony and halo masked the detection of any possible hemolysis. It is pointed out that the nitrogen source required for growth is supplied by the ingredients of the base agar (Columbia blood agar base) and not necessarily from the ammonium citrate ion.

EXPERIMENT 2

Lithium Chloride Concentration

Lithium chloride (LiCl) was used as early as 1960 at a concentration of 0.5 g/L as one of the selective agents for L. monocytogenes plating mediums. Since then, LiCl has been used in numerous other selective media at concentrations ranging from 5 to 15 g/L. In the first formulation of HCLA medium, pure cultures of L. monocytogenes grew well and produced distinct β-hemolysis on medium containing 15 g LiCl/L. When these experiments were expanded to the isolation of Listeria from fishery and dairy products, some strains produced hemolysis on HL plates but failed to exhibit hemolysis on HCLA agar. In subsequent experiments, hemolysis on HCLA agar was shown to be dependent upon lithium chloride concentration. Lithium chloride concentrations varying from 0 to 15 g/L in increments of 2.5 g were tested in HCLA. The optimum concentration of LiCl was 7.5 g/L. At this concentration, the hemolysis of the colonies was stronger, the colonies grew larger, and the blue-gray color was enhanced. When the LiCl concentrations were gradually increased from 7.5 to 15 g/L, the hemolytic zone, size, and the blue luster of the colonies decreased. Below the 5 g/L level, other background microorganisms were not inhibited. In the present study, certain Bacillus spp. were resistant to the effect of LiCl even at 7.5 g/L. The Bacillus colony morphology and type of hemolysis, however, were easily distinguished from L. monocytogenes. When large numbers of beta-hemolytic Bacillus spp. were resistant to the primary enrichments and HCLA agar, inoculation into a second selective UVM-2 usually eliminated the problem.

EXPERIMENT 3

Effect of Acriflavine and Moxalactam

Attempts were made to increase inhibition of Bacillus spp. by adding acriflavine or moxalactam to the medium at concentrations of 10, 25, and 50 mg/L, and 5, 10, 15, and 20 mg/L, respectively. Unfortunately, neither compound consistently inhibited all of the Bacillus spp. and acriflavine also inhibited the hemolytic activity of L. monocytogenes.

The experiment illustrates that only chemical agents that do not negatively impact the viability of L. monocytogenes should be used in the medium of the invention and agents such as acriflavine are to be avoided.

EXPERIMENT 4

Ceftazidime and Agar Concentrations

Ceftazidime has been used in various Listeria selective plating media at a concentration of 50 mg/L. In HCLA medium, Ceftazidime was evaluated at concentrations of 20, 30, 40, and 50 mg/L. A concentration of 20 mg/L was selected because it was as effective as 50 mg in inhibiting background microorganisms.

When the concentration of agar was 1.5%, L. monocytogenes often overgrew the hemolytic zones. Distinct zones of hemolysis were always observed when the agar content was increased to 2.0%.

EXPERIMENT 5

Comparison of Horse and Sheep Blood

β-hemolysis was compared on HCLA medium containing 2, 3, 4, and 5% horse and sheep blood. The blood was incorporated into an overlay poured over a base of HCLA without blood. Characteristic β-hemolytic zones around the colonies were most distinctive with 4% horse blood. Sheep blood was not as effective as horse blood but in most cases could be used if the concentration did not exceed 2%. At greater concentrations, the β-hemolysis on sheep blood was not evident.

EXPERIMENT 6

Incubation Temperature

Hemolytic activity by HCLA medium was compared at 20, 25, 30, and 35° C. Colonies did not exhibit consistent hemolysis when grown at 20, 25, or 30° C. Colonies always produced distinct β-hemolytic zones within 17–24 hours at 35° C.

COMPARATIVE EXAMPLE 2

HCLA was compared with OX media for recovery of *L. monocytogenes* from over 500 enrichment samples of fishery products. In no instance was *L. monocytogenes* recovered on OX, without also being recovered on HCLA.

Although testing was not extensive, the ease of using HCLA to detect *L. monocytogenes* in dairy products was also examined. Eight samples of unpasteurized milk and six samples of cheese, known to be contaminated with *L. monocytogenes*, (Dr. Kinde, University of California), were enriched in UVM and LEB. *L. monocytogenes* was readily recognized on HCLA plates from all of the samples. *L. monocytogenes* colonies from these products were the most sensitive to variation in LiCl and hemolysis was inhibited when concentrations exceeded 7.5 g/L.

Reactions of Other Listeria Species

*L. ivanovii* grew well on HCLA and produced beta-hemolysis within 17–24 h at 35° C. The zones of hemolysis, however, were larger than those observed with *L. monocytogenes*. Growth of *L. seeligeri* on HCLA was slower and hemolysis often was not evident until 48 h. Both *L. innocua* and *L. welshimeri* grew well on HCLA but did not hemolyze blood.

COMPARATIVE EXAMPLE 3

HCLA medium was compared to Oxford medium for the relative quantitative recovery of *Listeria monocytogenes* in the presence of high ritunbers of a variety of other microorganisms. Salmon samples were artificially contaminated with a pure culture of *L. monocytogenes* and then stored at 10° C. for 28–35 days. Total populations of microorganisms and *L. monocytogenes* populations were determined and ranged from $1.8 \times 10^7$ to $2.9 \times 10^8$ organisms per gram of salmon and *L. monocytogenes* populations ranged from $6.1 \times 10^4$ to $3.2 \times 10^7$ organisms per gram.

To compare recovery of HCLA to OX, 0.1 ml of a salmon sample was diluted with a liquid diluent and spread on the surface of 6 to 8 plates each of HCLA and OX media. A sterile, bent glass rod (hockey stick) of 2-mm diameter was used to spread the dilution as the plates were spun on a turntable. The plates were incubated at about 35° C. for 24 hours and the number of listeria colony forming units (CFU) were counted. Comparative counts from 5 samples are shown in Table 3.

In enumerating or identifying *L. monocytogenes* any food sample can be used Liquid diluents include sterile water, phosphate buffers and other dilients containing protein buffers such as peptones. As shown in Table 3 this method can be successfully used to enumerate and identify *L. monocytogenes* and therefore *L. monocytogenes* can be enumerated and identified without special enrichment procedures.

TABLE 3

|  | Media | |
| --- | --- | --- |
| Sample number | Oxford | HCLA |
| 4997 | TNTC[a] | TNTC |
| 4998–5002 | NOT DONE | NOT DONE |
| 5003 | 64[b] | 65 |
| 5004 | TNTC | TNTC |
| 5005–5008 | NOT DONE | NOT DONE |
| 5009 | 78 | 81 |
| 5010 | 161 | 180 |
| 5011 | NOT DONE | NOT DONE |
| 5012 | 66 | 70 |
| 5013–5015 | NOT DONE | NOT DONE |
| 5016 | 56 | 59 |

[a]TNTC = colonies were "too numerous to count".
[b]Mean number of colony forming units per plate from 6 to 8 replicate plates.

Analysis of variance showed that there was no significant difference (P<0.05) between the counts obtained with HCLA versus OX for samples 5003, 5009, 5012 and 5016. The counts for sample 5010, however, were significantly higher on HCLA than on OX. These results show the quantitative recovery of *L. monocytogenes* on HCLA media as good as, if not better than, on OX media.

While the invention has been particularly shown and described with reference to preferred embodiments thereof, it will be understood by those skilled in the art that changes in form and substance can be made thereto without departing from the spirit and scope of the invention.

For instance, the medium of the invention may be used to differentiate *L. monocytogenes* from Listeria species which do not produce hemolysis such as *L. innocua, L. murrayi, L. grayi* and *L. welshimeri* or to enumerate *L. monocytogenes* and *L. innocua* in a food or water sample. The medium can be used to differentiate *L. monocytogenes* from *L. seeligeri* and *L. ivanovii* due to differences in the hemolytic zone size, growth rate and colonial morphology.

The medium of the invention allows presumptive identification of *L. monocytogenes* from fishery products and fish, meat and meat products, poultry and poultry products, dairy products, water and vegetables.

What is claimed is:

1. A selective and differential medium devoid of esculin and acriflavine, which is specific for *Listeria monocytogenes* comprising:
   lithium chloride and one or more antibiotics and/or acceptable salts thereof, in amounts effective to selectively inhibit microbes other an Listeia, a growth enhancer for Listeria, and blood cells in amounts effective to produce β-hemolytic zones characteristic of *Listeria monocytogenes* colonies.

2. The medium of claim 1 wherein the growth enhancer comprises an iron-containing compound.

3. The medium of claim 1 wherein said antibiotics are selected from the group consisting of Colistin and Ceftazidime.

4. The medium of claim 1 wherein said red blood cells are selected from the group consisting of the blood of ovine, equine, and mixtures thereof.

5. A selective and differential medium for *Listeria monocytogenes*, devoid of esculin, and phenylethanol, comprising:
   i) an agar base layer comprising lithium chloride, antibiotics and/or acceptable salts thereof in amounts effective to selectively inhibit microbes other than Listeria, and
   ii) an agar overlay comprising blood in amounts effective to produce β-hemolytic zones characteristic of *L. monocytogenes* colonies.

6. The medium of claim 5, further comprising an iron-containing compound and the antibiotics comprise Colistin and Ceftazidime.

7. The medium of claim 5 wherein said agar overlay further comprises lithium chloride, Colistin and Ceftazidime in amounts effective to selectively inhibit microbes other than Listeria.

8. The medium of claim 5 wherein lithium chloride is present in amounts of 5 g/L to 15 g/L.

9. The medium of claim 8 wherein the lithium chloride concentration is 7.5 g/L.

10. The medium of claim 6 wherein the Ceftazidime is present in amounts a 20–50 mg/L.

11. The medium of claim 6 wherein the Ceftazidime is present in an amount of about 20 mg/L.

12. The medium of claim 5 wherein the blood overlay layer of the medium contains 2–5% blood.

13. A selective and differential medium for *Listeria monocytogenes*, consisting essentially of
   i) an agar base layer comprising lithium chloride, antibiotics and/or acceptable salts thereof in amounts effective to selectively inhibit microbes other than Listeria, and
   ii) an agar overlay comprising blood in amounts effective to produce β-hemolytic zones characteristic of *L. monocytogenes* colonies.

* * * * *